US011344640B2

(12) United States Patent
Anderson et al.

(10) Patent No.: US 11,344,640 B2
(45) Date of Patent: *May 31, 2022

(54) PORTABLE STERILIZATION AND DECONTAMINATION SYSTEM

(71) Applicant: Anderson Industries, LLC, Webster, SD (US)

(72) Inventors: Kory Anderson, West Fargo, ND (US); Daniel Ewert, Lake Park, MN (US); Joel Jorgenson, Fargo, ND (US)

(73) Assignee: Anderson Industries, LLC, Webster, SD (US)

( * ) Notice: Subject to any disclaimer, the term of this patent is extended or adjusted under 35 U.S.C. 154(b) by 50 days.

This patent is subject to a terminal disclaimer.

(21) Appl. No.: 16/385,681

(22) Filed: Apr. 16, 2019

(65) Prior Publication Data

US 2019/0321500 A1 Oct. 24, 2019

Related U.S. Application Data

(60) Provisional application No. 62/659,487, filed on Apr. 18, 2018.

(51) Int. Cl.
*A61L 2/07* (2006.01)
*A61L 2/10* (2006.01)
*A61L 2/04* (2006.01)

(52) U.S. Cl.
CPC .......... *A61L 2/07* (2013.01); *A61L 2/04* (2013.01); *A61L 2/10* (2013.01); *A61L 2202/11* (2013.01); *A61L 2202/14* (2013.01)

(58) Field of Classification Search
CPC ..... A61L 2/07; A61L 2/10; A61L 2/04; A61L 2202/14; A61L 2202/11; A61L 2/24;
(Continued)

(56) References Cited

U.S. PATENT DOCUMENTS 2,917,906 A 12/1959 Craig
6,489,052 B1 * 12/2002 Acker ................. H01M 8/0662
429/412
(Continued)

FOREIGN PATENT DOCUMENTS

WO 2008116165 9/2008
WO 2008116165 A2 9/2008
(Continued)

OTHER PUBLICATIONS

Transmittal of the International Search Report and Written Opinion of the International Searching Authority dated Nov. 14, 2019, for PCT/US 2019/027922, filed Apr. 17, 2019, pp. 8.
(Continued)

*Primary Examiner* — Regina M Yoo
(74) *Attorney, Agent, or Firm* — Womble Bond Dickinson (US) LLP

(57) ABSTRACT

A portable sterilization and decontamination system is described. The system includes a fuel cell configured to generate electricity and at least one of water or water vapor and a heating system operatively coupled to the fuel cell, the heating system to convert the energy to heat and provide the heat to a determined volume. The system further includes a humidifying system operatively coupled to the fuel cell, the humidifying system to utilize at least one of the electricity or the at least one of water or water vapor to produce moisture and provide the moisture to the determined volume and a control system operatively coupled to the fuel cell, the heating system and the humidifying system, the control system to monitor and control the fuel cell, the heating system and the humidifying system.

16 Claims, 7 Drawing Sheets

(58) Field of Classification Search
CPC .... A61L 2/20; A61L 2202/16; A61L 2202/25; Y02E 60/50; Y02B 90/10; H01M 2250/405; H01M 8/0618
See application file for complete search history.

(56) References Cited

U.S. PATENT DOCUMENTS

| | | | |
|---|---|---|---|
| 7,186,374 | B2 | 3/2007 | Zelina et al. |
| 7,518,502 | B2 | 4/2009 | Austin et al. |
| 8,206,490 | B2 | 6/2012 | Grasso et al. |
| 8,347,645 | B1* | 1/2013 | Miller ............... H01M 8/04149 62/236 |
| 8,372,169 | B2 | 2/2013 | Tsangaris et al. |
| 9,433,695 | B2 | 9/2016 | Aamodt et al. |
| 2003/0066830 | A1 | 4/2003 | Reed et al. |
| 2003/0157386 | A1* | 8/2003 | Gottmann ........... H01M 8/0662 429/465 |
| 2005/0129568 | A1* | 6/2005 | Kubby ................. A01M 1/2077 422/5 |
| 2008/0023322 | A1* | 1/2008 | Sinue .................. H01M 8/0656 204/252 |
| 2008/0220305 | A1* | 9/2008 | Carlstrom ......... H01M 8/04141 429/431 |
| 2013/0094994 | A1* | 4/2013 | Risch .................... B64D 11/02 422/26 |
| 2013/0126625 | A1* | 5/2013 | Groskreutz ............. F24F 5/001 237/8 A |
| 2013/0183749 | A1* | 7/2013 | Aamodt .................... A61L 2/22 435/287.1 |
| 2014/0317281 | A1 | 10/2014 | Hsu et al. |
| 2017/0175069 | A1 | 6/2017 | Baker, Jr. et al. |

FOREIGN PATENT DOCUMENTS

| | | |
|---|---|---|
| WO | 2017104927 | 6/2017 |
| WO | 02017104927 A1 | 6/2017 |

OTHER PUBLICATIONS

Transmittal of International Preliminary Report on Patentability for or PCT/US 2019/027922, filed Apr. 17, 2019, dated Oct. 20, 2020, pp. 6.

International Search Report and Written Opinion for PCT Application No. PCT/US2019/027922, dated Apr. 17, 2019, 8 pages.

* cited by examiner

PORTABLE STERILIZATION AND DECONTAMINATION SYSTEM

CROSS REFERENCE TO RELATED APPLICATIONS

This application claims the benefit of an earlier filing date of U.S. Provisional Patent Application No. 62/659,487, filed on Apr. 18, 2018, the disclosure of which is incorporated herein by reference in its entirety.

TECHNICAL FIELD

Aspects and implementations of the present disclosure relate to sterilization and decontamination systems.

BACKGROUND

Sterilization refers to processes that eliminate or deactivate forms of life and other biological agents present in a specified region. Sterilization systems may perform sterilization through various means including heat, chemicals, irradiation, pressure or filtration.

BRIEF DESCRIPTION OF THE DRAWINGS

Embodiments and implementations of the present disclosure will be understood more fully from the detailed description given below and from the accompanying drawings of various aspects and implementations of the disclosure, which, however, should not be taken to limit the disclosure to the specific embodiments or implementations, but are for explanation and understanding only.

DETAILED DESCRIPTION

Figure 1:
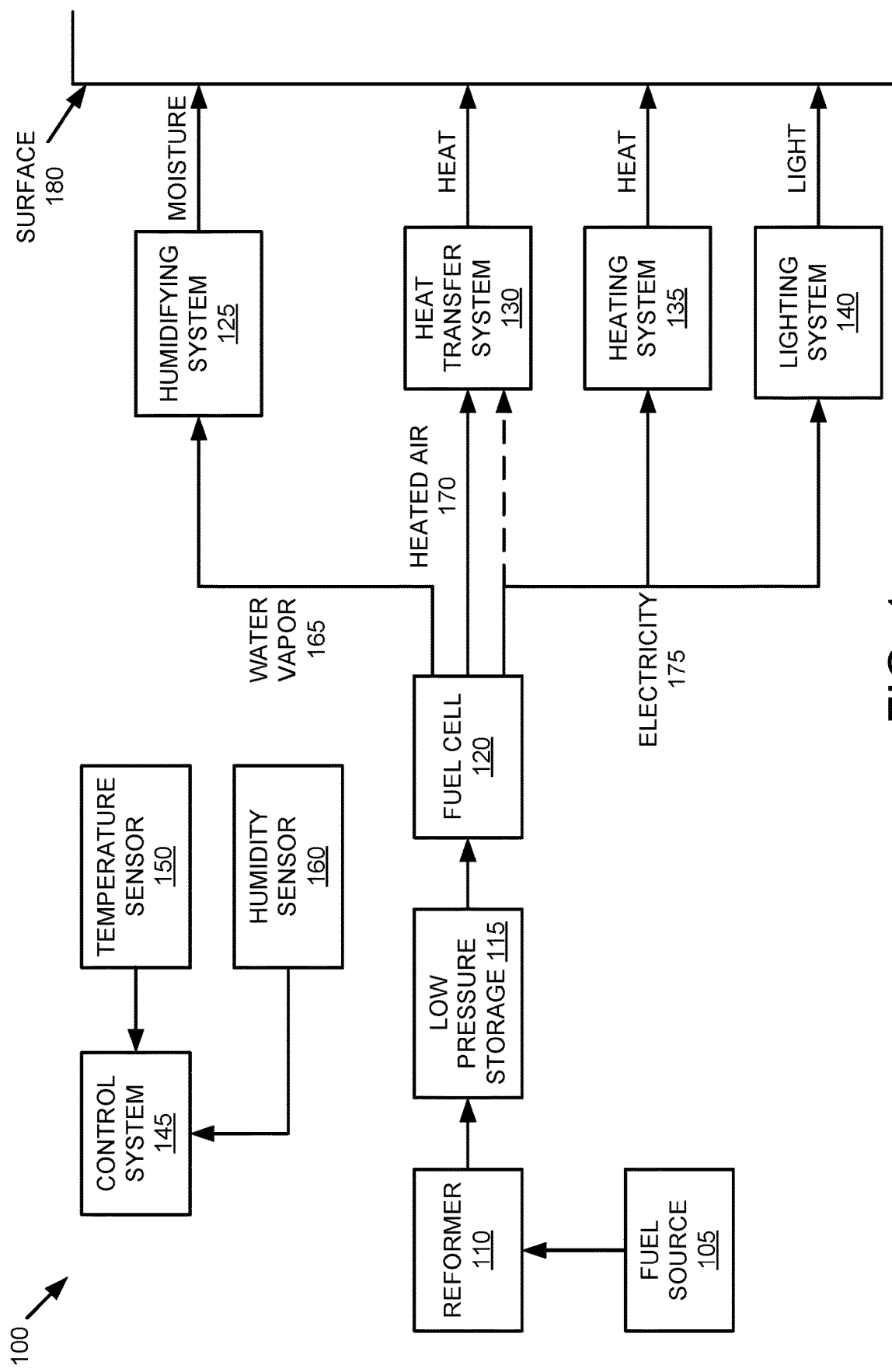
FIG. 1 illustrates an example configuration of a sterilization system in accordance with embodiments of the present disclosure.

Aspects and implementations of the present disclosure are directed to a portable sterilization and decontamination system (also referred to as "sterilization system" hereafter). Hotel rooms, apartment complexes, hospital rooms, and other areas have experienced highly publicized incidents of bed-bug infestations or other such undesirable events. Traditionally, treating infestations involved chemicals, which have multiple negative implications. First, over time, insects may develop a chemical resistance, rendering the treatment ineffective. Second, residue from chemical treatments may affect humans, animals, and plants adversely. Finally, care must be taken to prevent the drift of the applied chemicals to areas not intended for application.

By contrast, attacking infestations with a combination of heat, germicidal light, and humidity addresses many of the issues found in chemical treatments. Unlike chemical resistances, insects and animals are much less likely to develop a resistance to heat. For insects, bacteria, and viruses, heat kills in a known and predictable fashion. In a like fashion, humans, animals, and plants are not adversely affected with the momentary exposure to heat and humidity after a space has been treated. Finally, the use of blankets and insulating material easily confine the heat to only the spaces to be treated, leaving surrounding spaces unaffected.

To date, the heaters used for decontamination are heaters placed outside the physical structure of the infestation, with a series of ducting placed to transport the heat from the heater to the area of infestation. The heaters utilize an industrial engine (typically reciprocal engine using diesel, gasoline, or similar fuels, although turbine engines have been used). This treatment method is disruptive, since the size of the external heater and ducting as well as the large amount of noise produced is bothersome. In situations such as hotels and apartments, the externally-based heat treatment method may not be practical without affecting other people. Electric resistance heaters are also used and can be contained within a structure without excessive noise. However, the amount of electrical energy needed for a decontamination process may, and often does, exceed the electrical energy available within the structure, requiring extension cords that have to connect to an area that does have the necessary electrical energy.

Embodiments of the disclosure include a method and apparatus to sanitize and decontaminate physical spaces where infestations of insects, bacteria, virus, or molds might be present. One embodiment of the apparatus includes a hydrogen-based fuel cell, which provides heat, water/water vapor, and electricity. The electricity can be used to operate air movers, filters, resistance heaters, and sterilizing systems such as ultraviolet lighting. The entire system is portable and self-contained, and may sanitize and decontaminate an enclosed space (such as a hotel room) in less than a few hours. The system may be portable in that the sterilization system may be smaller, lighter and more easily transported than a conventional decontamination heater. The system may also be portable in that the sterilization system may be moved and operated within an interior space (e.g., a room) rather than being externally-based like a conventional decontamination heater.

Embodiments of the disclosure also include a portable system that has additional advantages in that it is roughly the size of a hotel service cart, can be rolled into a room, is discreet because no external ducting is needed to alert other guests, its operation is quiet due to the fuel cell technology, and the exhaust product is water/water vapor. Furthermore, this system can monitor temperatures throughout the room and display progress on a tablet, desktop or smartphone. Data are wirelessly transmitted to and stored on the cloud for future reference.

The portable system may include one or more of an electronic control system, portable removal tanks containing a gaseous hydrogen, a liquid fuel, a fuel reformer to convert a liquid fuel to gaseous hydrogen, a fuel cell stack to convert hydrogen to heat and electricity, and a combination of air movers and lighting strips capable of producing wavelengths in the short wavelength ultraviolet range capable of sterilization and sanitation.

The liquid fuel may be any fuel suitable for reformation to hydrogen, including (but not limited to) methanol, ethanol, diesel, gasoline, kerosene, or similar hydrocarbon fuel. In a preferred embodiment, the liquid fuel is a combination of methanol and de-ionized water. This mixture is not flammable when chilled to below 50 degrees Fahrenheit, which greatly lowers the danger of using a liquid fuel in interior structures. The containers of the liquid fuel may be placed on thermally controlled pads that provide known temperatures for the containers.

The output of the fuel reformer provides gaseous fuel to the fuel cell stack, which converts the gaseous fuel to a combination of electricity, heat, and water vapor. The water vapor and heat can be used in combination to create conditions within the enclosed space sufficient to kill insect infestation without adversely affecting furnishings or personal assets. If additional heat is desired beyond the radiated heat generated by fuel cell stack, the electricity provided by the fuel cell may be used to power supplemental heaters. The electronic control may adjust the temperature of the output air and the humidity created by the water vapor to realize any point on the psychrometric chart.

The air movers associated with the sterilization and decontamination system provides a uniform temperature distribution throughout the interior structure and may be powered by the electricity produced by the fuel cell. Temperature probes located throughout the interior structure and connected to the electronics control system provides assurance that the entire interior space is thermally controlled to conditions that meet system needs for killing insects.

To further disinfect, the system provides short wavelength ultraviolet light in the 230 nm to 280 nm spectrum. Light emitted in these wavelengths are lethal to microorganisms due to effects at the cellular level, and may be produced with light emitting diodes or light bulbs. In a preferred embodiment, the ultraviolet light is produced by a series of lights that produced uniform lighting over all surfaces for disinfection.

Certain embodiments of the disclosure produce superior results over conventional designs by its compact size and discreet operation. The relative silence of the system means that the adjacent rooms to a room being treated may be occupied without annoyance. The use of light and heat, each of which has no residue, means that a treated room can be used shortly after the disinfection process has been completed. Finally, the cost of operation, due to the relatively low cost of liquid fuels compared to chemical treatments and insecticides, produce a cost-effective solution for disinfection.

FIG. 1 illustrates an example configuration of a sterilization system 100 in accordance with embodiments of the present disclosure. The sterilization system 100 may include a fuel source 105, a fuel cell 120, a humidifying system 125, a heating system 135 and a control system 145.

The control system 145 may be operatively coupled to the fuel source 105, the fuel cell 120, the humidifying system 125 and the heating system 135. The control system 145 may also be operatively coupled to one or more sensors include one or more temperature sensors 150. In embodiments, the temperature sensor 150 may measure a temperature of a volume of space (e.g., a determined volume) being heated by the sterilization system 100. The temperature sensor 150 may provide the measured temperatures to the control system 145. The control system 145 may utilize the measured temperatures to adjust parameters and/or operations of the sterilization system 100, as will be described in further detail below.

Sterilization system 100 may further include one or more humidity sensors 160. In embodiments, the humidity sensor 160 may measure the humidity of a volume of space being humidified by the sterilization system 100. The humidity sensor 160 may be operatively coupled to the control system 145 to provide the measured humidity to the control system 145. The control system 145 may utilize the measured humidity to adjust parameters and/or operations of the sterilization system 100, as will be described in further detail below.

The fuel source 105 is a storage system for the fuel that is to be provided to the fuel cell 120. The fuel source 105 may store a hydrocarbon fuel, such as hydrogen, carbon monoxide, methanol, methane, gasoline, diesel, jet fuel or other hydrocarbon fuels. In some embodiments, fuel source 105 may be a compressed air cylinder storing pure hydrogen. The fuel source 105 is operatively coupled to the fuel cell 120 to provide fuel from fuel source 105 to the fuel cell 120. For example, one or more hoses or tubes may be coupled between the fuel source 105 and the fuel cell 120 to provide the fuel to the fuel cell 120. In embodiments, one or more pumps may be utilized to move the fuel from the fuel source 105 to the fuel cell 120.

In some embodiments, a reformer 110 may be operatively coupled to fuel source 105. The reformer 110 may be operatively coupled between the fuel source 105 and the fuel cell 120 to extract hydrogen from the hydrocarbon fuel provided by fuel source 105. An example reformer 110 may be a steam reformer that is configured to cause a reaction between steam at a high temperature and pressure with a hydrocarbon fuel source, such as methanol, in the presence of a nickel catalyst. In embodiments, other types of reformers 110 may be used to extract hydrogen from a hydrocarbon fuel.

In embodiments, upon extraction of the hydrogen from the hydrocarbon fuel by the reformer 110, the extracted hydrogen may be provided to a low pressure storage 115 that is operatively coupled to the reformer 110. Low pressure storage 115 may be a storage system, such as a storage tank or container, which is configured to store the extracted hydrogen at low pressures of approximately one atmosphere. The low pressure storage 115 may provide additional advantages to the sterilization system 100 since storing the extracted hydrogen at a low pressure greatly reduces the risk of explosion and, in the event that the low pressure storage 115 is ruptured, the hydrogen will be released at a much slower rate than a pressurized hydrogen storage system. In some embodiments, rather than storing the extracted hydrogen at the low pressure storage 115, the extracted hydrogen may be provided directly from reformer 110 to fuel cell 120.

The low pressure storage 115 may be operatively coupled to the fuel cell 120 to provide the extracted hydrogen stored at the low pressure storage 115 to the fuel cell 120. The fuel cell 120 converts energy from the fuel through an electrochemical reaction of the fuel with oxygen or another oxidizing agent. The fuel cell 120 can include an anode, an electrolyte and a cathode. At the anode a catalyst oxidizes the fuel, turning the fuel into positively charged ions and negatively charged electrons. The positively charged ions pass through the electrolyte, while the negatively charged electrons cannot pass through the electrolyte. The negatively charged electrons travel through a wire to create electric current. The negatively charged electrons are then reunited with the positively charged ions at the cathode, where the negatively charged electrons react with the positively charges ions to produce water vapor and heat. Various types of fuel cells 120 may be used in various embodiments of the disclosure depending on a type of fuel of the fuel source. Examples of types of fuel cells that may be used include, but are not limited to, proton exchange membrane fuel cells (PEMFCs), phosphoric acid fuel cells (PAFCs), solid acid fuel cells (SAFCs), alkaline fuel cells (AFC), solid oxide fuel cells (SOFCs), molten carbonate fuel cells (MCFCs) and electric storage fuel cells. The fuel cell 120 may generate electricity 175 using either a pure hydrogen fuel source or extracted hydrogen from a hydrocarbon fuel. Other byproducts of the reaction within the fuel cell 120 may include water vapor 165 and thermal energy (e.g., heated air 170). Embodiments of the disclosure may capture and utilize these byproducts, providing further advantages over a conventional sterilization system.

In embodiments, the heating system 135 may be a radiant heater that emits infrared radiation. In an embodiment, the heating system 135 may be a convection heater that utilizes a heating element to heat the air in contact with the heating element by thermal conduction. In some embodiments, the heating system 135 may be a heat pump that utilizes an electrically driven compressor to operate a refrigeration cycle that extracts heat energy from outdoor air, the ground or ground water, and moves the heat into the space to be warmed. In embodiments, the heating system 135 may be an electrical resistance heating element. In embodiments, the heating system 135 may be an induction heater configured to generate heat by electromagnetic induction. In an embodiment, the heating system 135 may be any device that converts electricity 175 generated by fuel cell 120 into thermal energy.

The water vapor 165 generated by fuel cell 120 may be provided to a humidifying system 125 operatively coupled to the fuel cell 120. The humidifying system 125 may utilize the water vapor 165 provided by the fuel source 120 to add moisture to an outflow airstream of the sterilization system system 100. In some embodiments, humidifying system 125 may also receive electricity 175 from fuel cell 120 to power one or more components of humidifying system 125. In embodiments, humidifying system 125 may be a boiler configured to utilize the electricity 175 and water vapor 165 provided by the fuel cell 120 to produce steam that is introduced as moisture into the outflow airstream of the sterilization system 100. In some embodiments, the humidifying system 125 may be a membrane humidifier that adds moisture into the outflow airstream by flowing the airstream along a wetted membrane. Other examples of humidifying systems 125 that may be utilized by the sterilization system 100 may include evaporative humidifiers, natural humidifiers, vaporizers, impeller humidifiers, ultrasonic humidifiers, drum humidifiers, disc wheel humidifiers, bypass flow-through humidifiers, spray mist humidifiers and any other type of humidifier configured to add moisture to the outflow airstream.

In some embodiments, the heated air 170 generated by the reaction that takes place in the fuel cell 120 to generate electricity 175 may also be used as a heat source to supplement the heat generated by heating system 135. The heated air 170 may be provided to a heat transfer system 130 operatively coupled to the fuel cell 120. The heat transfer system 130 may be configured to move the heated air 170 from the fuel cell 120 to a determined volume of space. In an embodiment, the heat transfer system 130 may include one or more fans that move the heated air 170. In embodiments, the heat transfer system 130 may include one or more pumps to move the heated air 170. In some embodiments, the heat transfer system 130 may include a radiator that transfers the thermal energy of the heated air 170 to a desired volume of space. In embodiments, electricity 175 generated by the fuel cell 120 may be provided to the heat transfer system 130 to power various components of the heat transfer system 130. For example, the electricity 175 may be used to power the fans, pumps, etc. of the heat transfer system 130. In some embodiments, the heated air 170 moved by the heat transfer system 130 may be combined in the outflow airstream of the sterilization system 100 with the heat generated by heating system 135.

In embodiments, the electricity 175 generated by fuel cell 120 may be provided to a lighting system 140 operatively coupled to the fuel cell 120. In embodiments, the lighting system 140 may be an ultraviolet germicidal irradiation system that uses short-wavelength (e.g., between 230-280 nanometers) ultraviolet (UV) light to kill or inactivate microorganisms. The lighting system 140 may include one or more lamps or light emitting diodes (LEDs) to generate the UV light using the electricity 175 from the fuel cell 120.

The heat, moisture and/or UV light generated by the sterilization system 100 may be provided to a determined volume for sterilization or decontamination of the determined volume. In some embodiments, the determined volume may be a surface 180 of an interior space. For example, the surface 180 may be a wall, ceiling or floor of a room that requires sterilization or decontamination. In embodiments, one or more components (e.g., fuel cell 120, humidifying system 125, heating system 135, lighting system 140, etc.) of the sterilization system 100 may be mounted to a portable chassis to form a portable unit, as will be described in further detail below.

Figure 2:
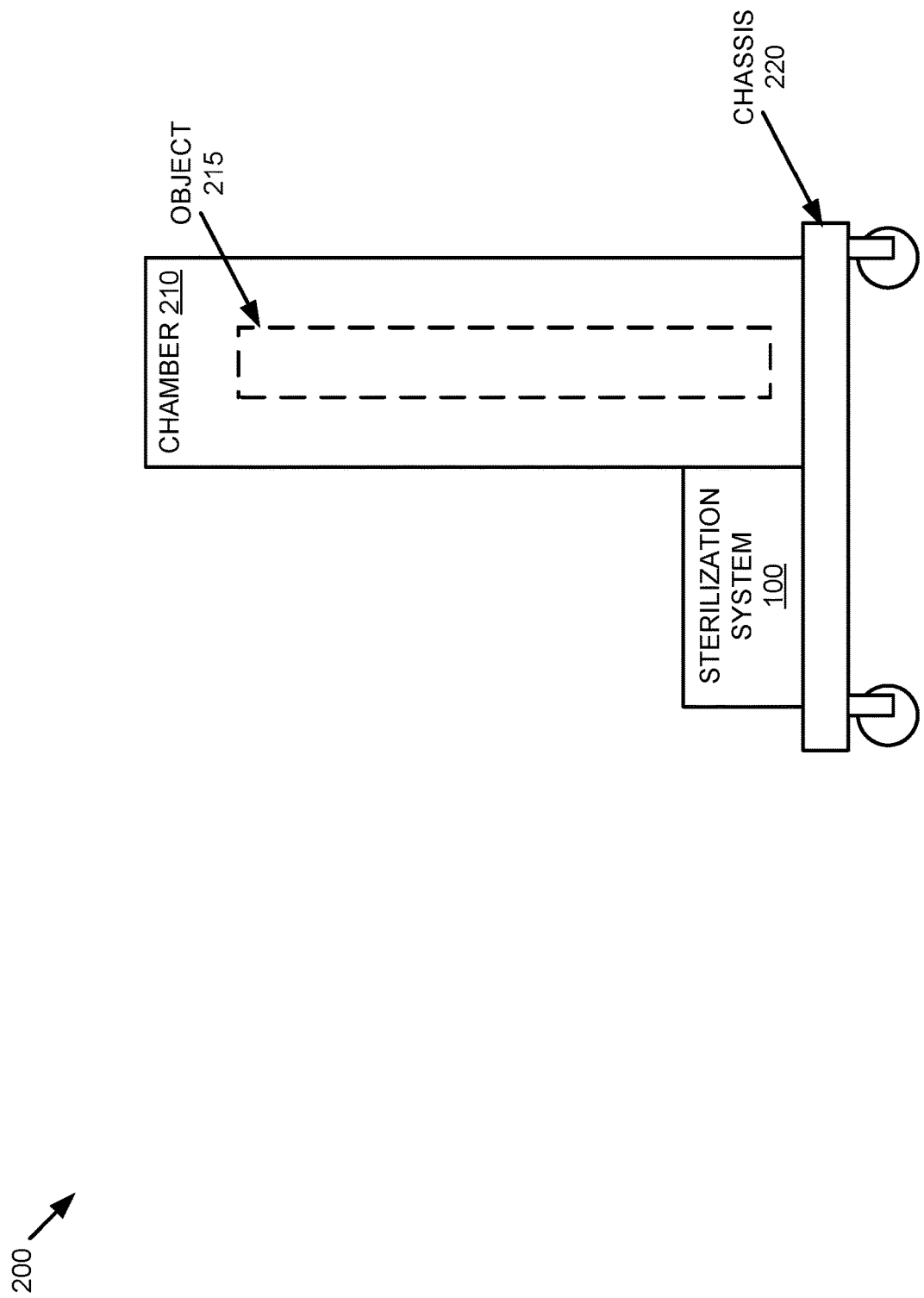
FIG. 2 is an illustration of an example portable sterilization system including a sterilization chamber in accordance with an embodiment of the disclosure.

FIG. 2 is an illustration of an example portable sterilization system 200 including a sterilization chamber in accordance with an embodiment of the disclosure. The portable unit 200 includes a sterilization system 100 as previously described at FIG. 1. The sterilization system 100 may be mounted to a portable chassis 220 that includes wheels, rollers or any other types of components to facilitate the movement of sterilization system 100.

In some embodiments, the portable unit 200 may include a chamber 210 for the sterilization and decontamination of objects. The chamber 210 may be insulated to prevent heat, moisture and/or light generated by the sterilization system 100 from exiting the chamber 210. In embodiments, one or more components of the sterilization system 100 may be located within chamber 210. For example, one or more lamps/LEDs of the lighting system (not shown) of the sterilization system 100 may be located within chamber 210 to illuminate the interior of chamber 210.

An object 215 that is to be decontaminated or sterilized may be placed within the chamber 210. For example, a hotel mattress may be placed within chamber 210 for sterilization and decontamination. The heat, moisture and/or light generated by the sterilization system 100 may then be provided to the chamber 210 for the sterilization and decontamination of the object 215. A control system of the sterilization system 100 may monitor the conditions (e.g., temperature, humidity, etc.) by receiving data from one or more sensors (not shown) located in chamber 210. The control system may make adjustments to the operation of the sterilization system 100 so that the environment within chamber 210 is at a desired temperature and/or humidity level.

Figure 3:
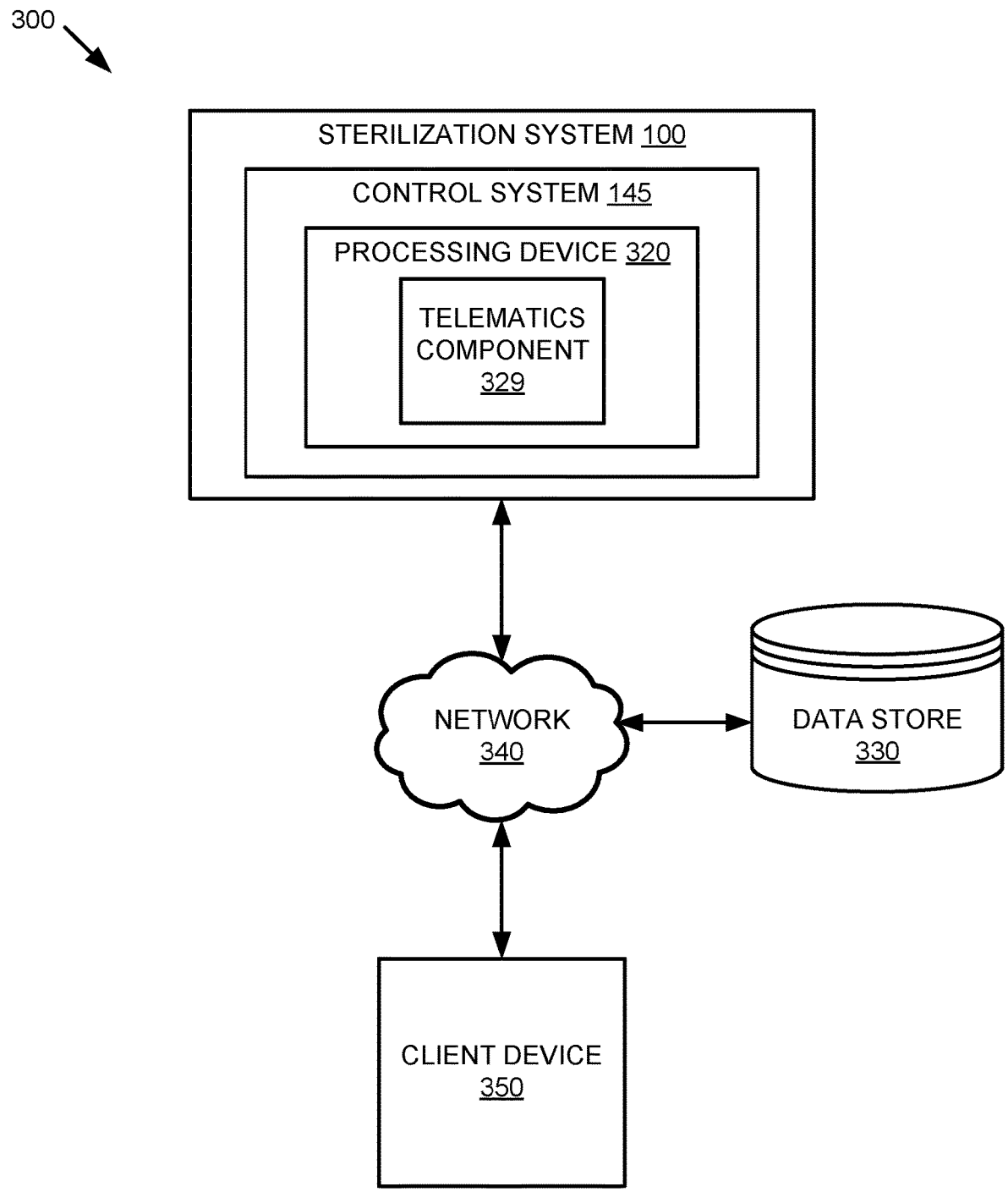
FIG. 3 is a block diagram that illustrates an example of a telematics system in accordance with an embodiment of the present disclosure.

FIG. 3 is a block diagram that illustrates an example of a telematics system 300, in accordance with an embodiment of the present disclosure. The telematics system 300 may include control system 145 of the sterilization system 100, as previously described with respect to FIGS. 1 and 2. The control system 145 includes a processing device 320 that executes a telematics component 329. In embodiments, the control system 145 may be operatively coupled to a data store 330 and a client device 350 via a network 340. In some embodiments, the data store 330 may reside in the control system 145.

The network 340 may be a public network (e.g., the internet), a private network (e.g., a local area network (LAN) or wide area network (WAN)), or a combination thereof. In one embodiment, network 340 may include a wired or a wireless infrastructure, which may be provided by one or more wireless communications systems, such as a WiFi™ hotspot connected with the network 340 and/or a wireless carrier system that can be implemented using various data processing equipment, communication towers (e.g. cell towers), etc.

The client device 350 may be a computing device, such as a personal computer, laptop, cellular phone, personal digital assistant (PDA), gaming console, tablet, etc. In embodiments, the client device 350 may be associated with a user of the sterilization system 100.

The data store 330 may be a persistent storage that is capable of storing data (e.g., parameters associated with a sterilization system 100, as described herein). A persistent storage may be a local storage unit or a remote storage unit. Persistent storage may be a magnetic storage unit, optical storage unit, solid state storage unit, electronic storage units (main memory), or similar storage unit. Persistent storage may also be a monolithic/single device or a distributed set of devices.

In embodiments, data store 330 may be a central server or a cloud-based storage system including a processing device (not shown). The central server or the cloud-based storage system may be accessed by control system 145 and/or client device 350. Parameters from the sterilization system 100 may be transmitted to the data store 330 for storage. In embodiments, upon receipt of the parameters, the data store 330 may transmit the parameters to client device 350. In some embodiments, the parameters stored at the data store may be accessed by client device 350 via a user interface. For example, the data store 330 may generate a graphical user interface (GUI) to present the parameters of the sterilization system 100 to client device 350. In embodiments, client device 350 may provide adjustments to one or more parameters of the sterilization system 100 to the data store 330. In some embodiments, upon receipt of the adjustments, the data store 330 may transmit the adjustments to the parameters to control system 145. In some embodiments, the adjustments to the parameters may be accessed by control system 145 via a user interface.

In embodiments, telematics component 329 may transmit parameters of a sterilization system to client device 350. Telematics component 329 may receive, from client device 350, one or more adjustments to one or more parameters of the sterilization system 100.

Figure 4:
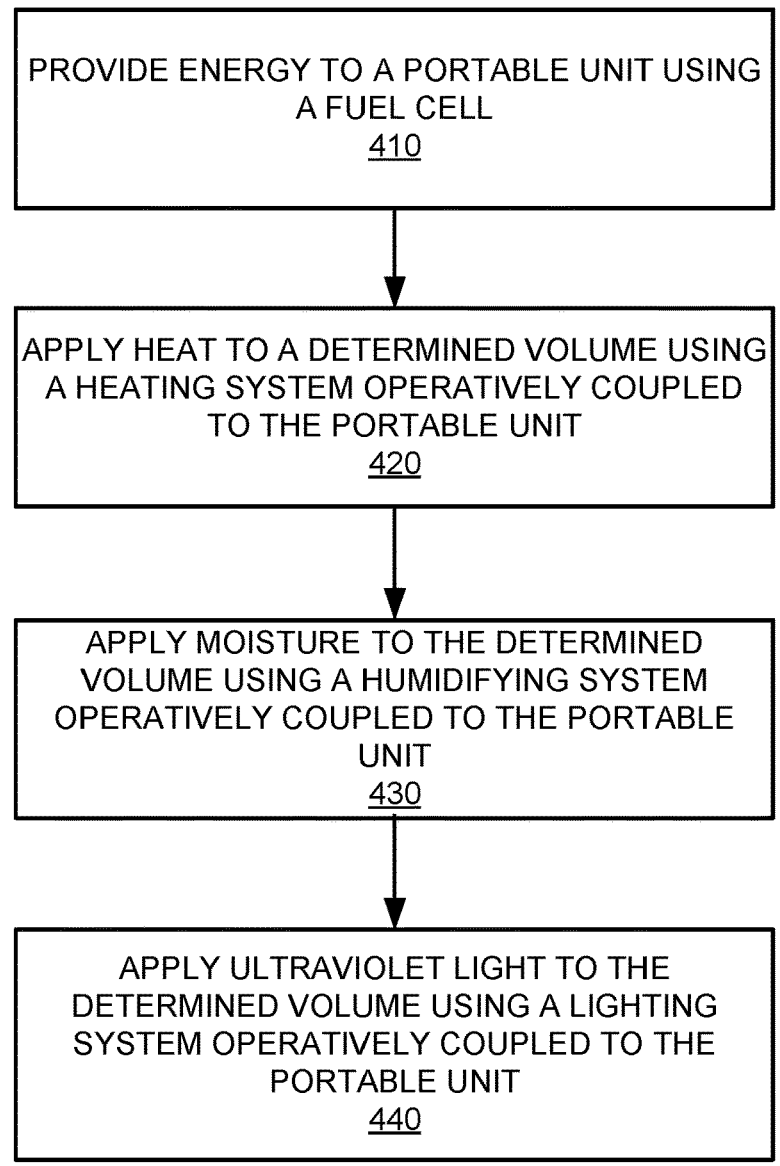
FIG. 4 depicts a flow diagram of a method for portable sterilization and decontamination using a fuel cell in accordance with one implementation of the present disclosure.

FIG. 4 depicts a flow diagram of a method 400 for portable sterilization and decontamination using a fuel cell in accordance with one implementation of the present disclosure. In embodiments, various portions of method 400 may be performed by sterilization system 100 of FIG. 1.

With reference to FIG. 4, method 400 illustrates example functions used by various embodiments. Although specific function blocks ("blocks") are disclosed in method 400, such blocks are examples. That is, embodiments are well suited to performing various other blocks or variations of the blocks recited in method 400. It is appreciated that the blocks in method 400 may be performed in an order different than presented, and that not all of the blocks in method 400 may be performed.

At block 410, energy is provided to a portable sterilization system using a fuel cell. The fuel cell may receive hydrogen and generate electricity, thermal energy and water vapor as byproducts of the reaction within the fuel cell. The electricity, thermal energy and/or water vapor may be provided to various components (e.g., heating system, humidity system, lighting system, etc.) of the portable sterilization system.

At block 420, heat is applied to a determined volume of space using a heating system operatively coupled to the fuel cell. The heating system may receive electricity from the fuel cell and convert the electricity to heat, as previously described. In some embodiments, heat may also be provided to the determined volume by a heat transfer system that provides thermal energy generated by the fuel cell to the determined volume. In embodiments, the determined volume may be one or more surfaces of an interior space. In an embodiment, the determined volume may be a sterilization chamber.

At block 430, moisture is applied to the determined volume using a humidifying system operatively coupled to the fuel cell. The humidifying system may convert the electricity and/or water vapor generated by the fuel cell to produce moisture for application to the determined volume, as previously described. At block 440, ultraviolet light is applied to the determined volume using a lighting system operatively coupled to the fuel cell, as previously described.

Figure 5:
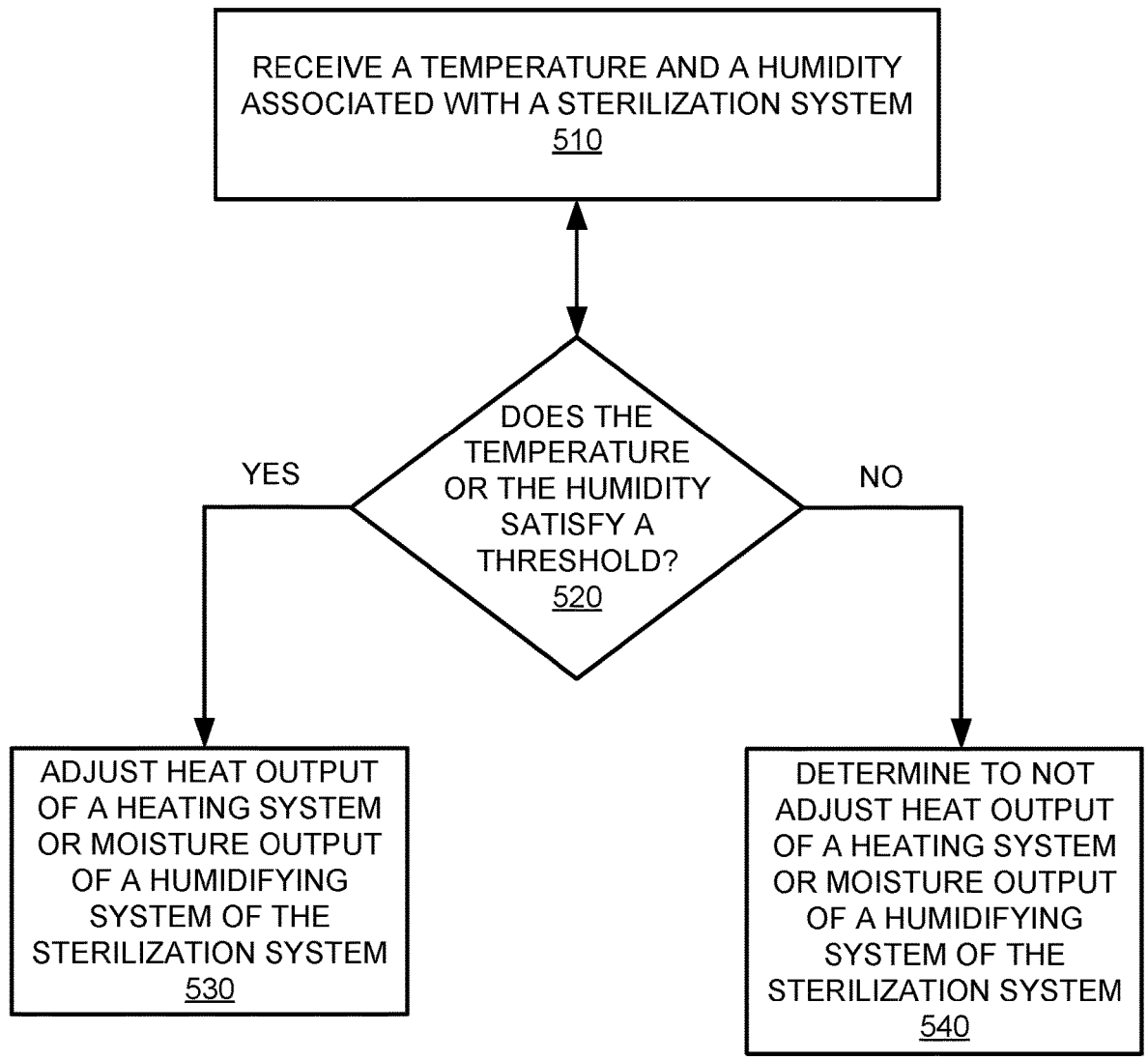
FIG. 5 depicts a flow diagram of a method for controlling a portable sterilization system in accordance with implementations of the present disclosure.

FIG. 5 depicts a flow diagram of a method 500 for controlling a portable sterilization system in accordance with implementations of the present disclosure. In embodiments, various portions of method 500 may be performed by control system 145 of FIGS. 1 and 2.

With reference to FIG. 5, method 500 illustrates example functions used by various embodiments. Although specific function blocks ("blocks") are disclosed in method 500, such blocks are examples. That is, embodiments are well suited to performing various other blocks or variations of the blocks recited in method 500. It is appreciated that the blocks in method 500 may be performed in an order different than presented, and that not all of the blocks in method 500 may be performed.

At block 510, a control system (e.g., processing device 702) receives a temperature and a humidity associated with a sterilization system. In some embodiments, the temperature and humidity associated with the sterilization system may correspond to a temperature and humidity of a determined volume, such as a surface of an interior space or a sterilization chamber. In embodiments, the control system may receive the temperature from one or more temperature sensors of the sterilization system. In some embodiments, the control system may receive the humidity from one or more humidity sensors of the sterilization system.

At block 520, the control system determines if the temperature and/or the humidity received at block 510 satisfies a threshold. In embodiments, the threshold may correspond to a temperature value. In embodiments, the temperature may satisfy the threshold if the temperature is greater than or equal to the threshold. For example, if the threshold is 110 degrees and the temperature received at block 510 is 112 degrees, then the temperature satisfies the threshold. In some embodiments, the temperature may satisfy the threshold if the temperature is less than or equal to the threshold. For example, if the threshold is 72 degrees and the temperature received at block 510 is 68 degrees, then the temperature satisfies the threshold. In an embodiment, multiple thresholds may be used to create a range of temperatures. For example, a first threshold may be used that specifies a temperature less than or equal to 65 degrees satisfies the first threshold and a second threshold may be used that specifies a temperature greater than or equal to 75 degrees satisfies the second threshold. Accordingly, if the received temperature is outside of the specified temperature range (e.g., is less than or equal to 65 degrees or greater than or equal to 75 degrees), then the temperature satisfies the threshold.

In some embodiments, the threshold may correspond to a humidity value. In embodiments, the humidity may satisfy the threshold if the humidity is less than or equal to the threshold. In an embodiment, the humidity may satisfy the threshold if the humidity is greater than or equal to the threshold. In some embodiments, multiple thresholds may be used for temperature and humidity. For example, the control system may utilize a temperature threshold corresponding to a temperature value and a humidity threshold corresponding to a humidity value. In embodiments, the threshold may be provided via a user interface of the control system. In some embodiments, the threshold may be provided via a temperature regulating device, such as a thermostat.

If the temperature and/or humidity satisfies the threshold, at block 530 the control system adjusts the heat output of a heating system and/or the moisture output of a humidifying system of the sterilization system. For example, if the temperature received at block 510 is too high (e.g., is greater than the threshold at block 520), then the control system may decrease the heat output of the heating system. In another example, if the temperature received at block 510 is too low (e.g., is less than the threshold at block 520), then the control system may increase the heat output of the heating system.

In embodiments, if the humidity is too high, then the control system may decrease the moisture output of a humidifying system of the sterilization system. In an embodiment, if the humidity is too low, then the control system may increase the moisture output of the humidifying system.

In embodiments, the control system may adjust the heat output and/or moisture output based on a psychometric chart. The psychometric chart may be a graphical representation of parameters of moist air at atmospheric pressure. Examples of parameters that may be utilized by the control system include dry-bulb temperature, wet-bulb temperature, dew point temperature, relative humidity and humidity ratio. The control system may determine one or more of the parameters of the psychometric chart utilizing one or more sensors operatively coupled to the control system.

If the control system determines the temperature does not satisfy the threshold, at block 540 the control system determines to not adjust the heat output of the heating system and/or the moisture output of the humidifying system of the sterilization system.

Figure 6:
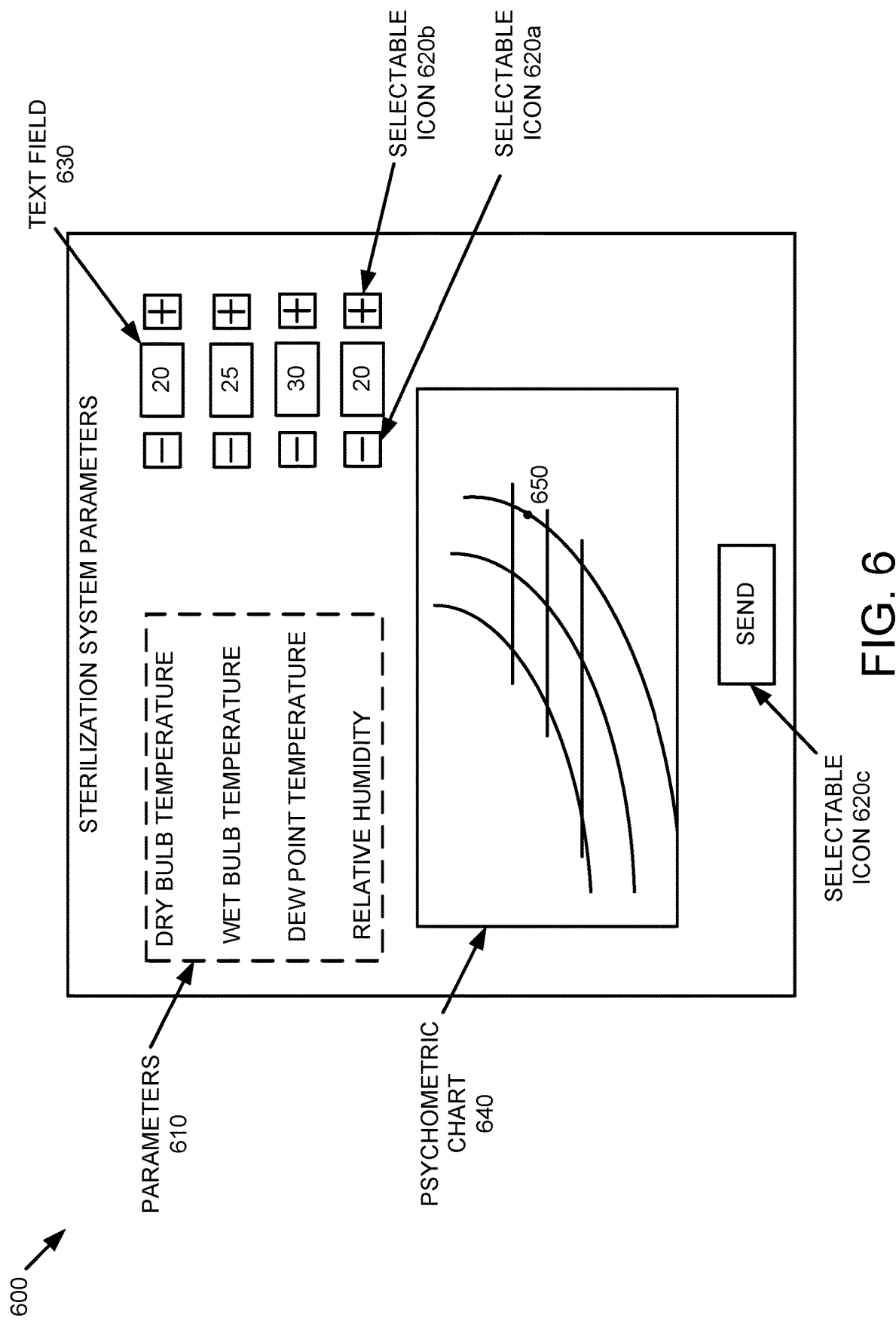
FIG. 6 is an illustration of an example of a user interface to present one or more parameters of a portable sterilization system in accordance with embodiments of the disclosure.

FIG. 6 is an illustration of an example of a user interface 600 to present one or more parameters of a portable sterilization system in accordance with embodiments of the disclosure. As previously described, in some embodiments a user interface may be generated to present the parameters of a sterilization system. In embodiments, the user interface 600 may be generated by control system 145. In an embodiment, the user interface 600 may be generated by data store 330. In some embodiments, the user interface 600 may be generated by client device 350.

The user interface 600 may include information associated with one or more parameters 610 of the sterilization system. Referring to FIG. 6, the parameters 610 presented in the user interface 600 correspond to the dry bulb temperature, the wet bulb temperature, the dew point temperature and the relative humidity of a determined volume associated with the sterilization system. It should be noted that the parameters 610 included in user interface 600 are for illustrative purposes only and embodiments of the disclosure may display any combination of parameters of a sterilization system.

Each of parameters 610 may include a corresponding text field 630. Values presented in text fields 630 may correspond to the received parameters from the sterilization system. In embodiments, text fields 630 may be selected and an adjustment to the parameter may be entered into the text field 630. For example, a user may select text field 630 that corresponds to the dry bulb temperature and enter an adjustment to adjust the dry bulb temperature from 20 to 25. In embodiments, upon receiving the adjustment, the control system may query a psychometric chart to determine what adjustments are to be made to the heat output of a heating system and/or moisture output of a humidifying system such that the adjusted parameter is attained.

In some embodiments, user interface 600 may be presented on a display of a control system of the sterilization system and the input to adjust the parameters of the sterilization system may be received via the control system. In some embodiments, user interface 600 may be presented on a display of a client device and the input to adjust the parameters of the sterilization system may be made via the client device. The adjustments may then be sent to the control system of the sterilization system via a telematics system, as previously described at FIG. 3.

User interface 600 may also include selectable icons 620a, 620b and 620c. Selectable icons 620a, 620b and 620c may be selected by a control system and/or client device to perform a desired action. For example, selectable icon 620a may decrease the value of a corresponding parameter when selected. Selectable icon 620b may increase the value of the corresponding parameter when selected. In embodiments, selectable icon 620c may transmit (e.g., send) a message including adjustments to be made to the parameters of the sterilization system.

In some embodiments, user interface 600 may include a psychometric chart 640. In embodiments, a point 650 on the psychometric chart 640 may be selected and the control system of the sterilization system may make adjustments to the parameters of the sterilization system based on the selected point 650. For example, a user may select a particular point 650 on a psychometric chart 640 via a control system or client device. Upon receiving the selection, the control system may adjust the parameters of the sterilization system based on the selected point 650 on the psychometric chart 640.

Figure 7:
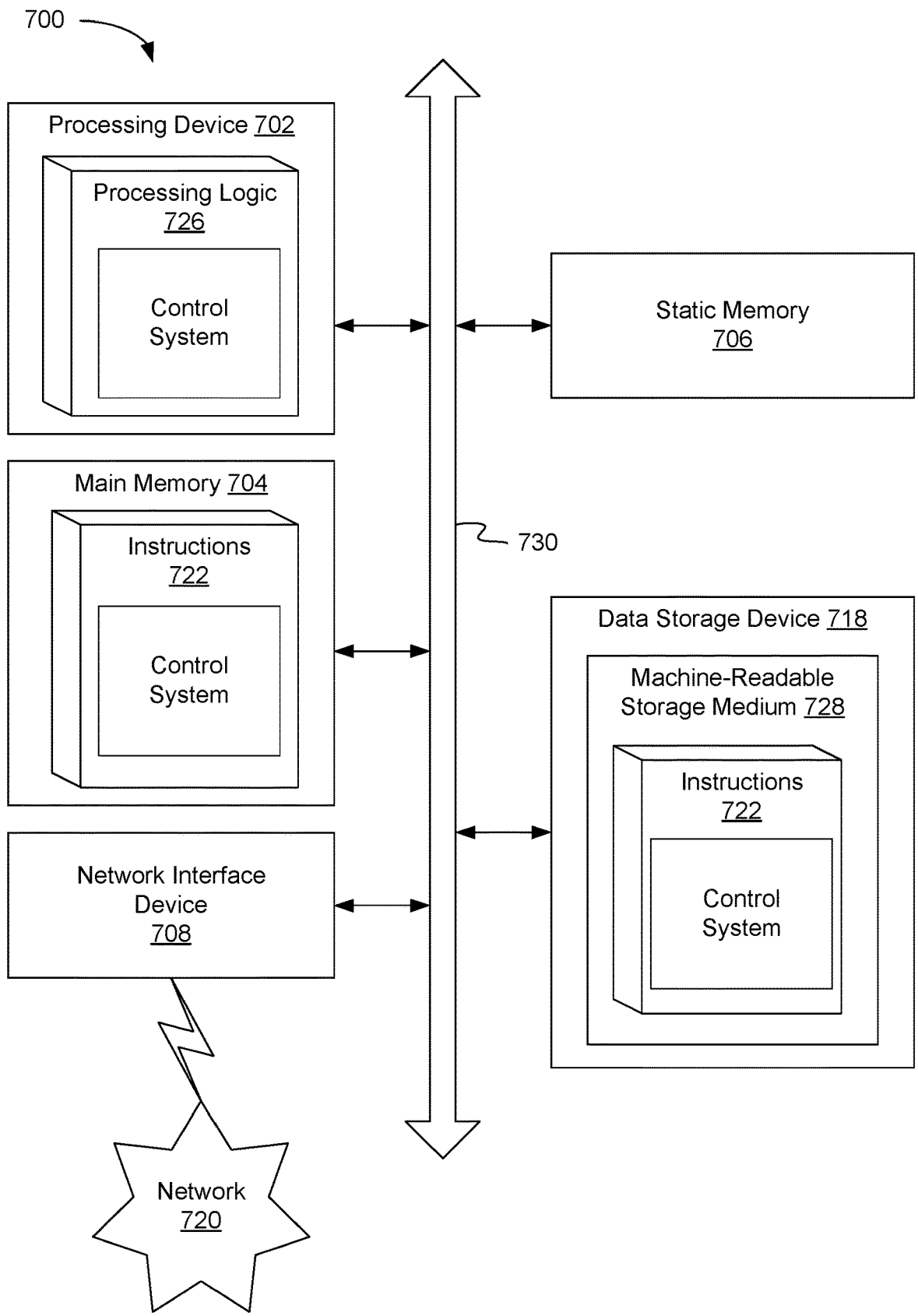
FIG. 7 illustrates a diagrammatic representation of a machine in the example form of a computer system.

FIG. 7 illustrates a diagrammatic representation of a machine in the example form of a computer system 700 within which a set of instructions, for causing the machine to perform any one or more of the methodologies discussed herein, may be executed. In alternative embodiments, the machine may be connected (e.g., networked) to other machines in a local area network (LAN), an intranet, an extranet, or the Internet. The machine may operate in the capacity of a server or a client machine in a client-server network environment, or as a peer machine in a peer-to-peer (or distributed) network environment. The machine may be a personal computer (PC), a tablet PC, a web appliance, a server, or any machine capable of executing a set of instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein. In one embodiment, computer system 700 may be representative of a server configured to control the operations of sterilization system 100.

The exemplary computer system 700 includes a processing device 702, a user interface display 713, a main memory 704 (e.g., read-only memory (ROM), flash memory, dynamic random access memory (DRAM), a static memory 706 (e.g., flash memory, static random access memory (SRAM), etc.), and a data storage device 718, which communicate with each other via a bus 730. Any of the signals provided over various buses described herein may be time multiplexed with other signals and provided over one or more common buses. Additionally, the interconnection between circuit components or blocks may be shown as buses or as single signal lines. Each of the buses may alternatively be one or more single signal lines and each of the single signal lines may alternatively be buses.

Processing device 702 represents one or more general-purpose processing devices such as a microprocessor, central processing unit, or the like. More particularly, the processing device may be complex instruction set computing (CISC) microprocessor, reduced instruction set computer (RISC) microprocessor, very long instruction word (VLIW) microprocessor, or processor implementing other instruction sets, or processors implementing a combination of instruction sets. Processing device 702 may also be one or more special-purpose processing devices such as an application specific integrated circuit (ASIC), a field programmable gate array (FPGA), a digital signal processor (DSP), network processor, or the like. The processing device 702 is configured to execute processing logic 726, which may be one example of sterilization system 100 as shown in FIG. 1, for performing the operations and blocks discussed herein.

The data storage device 718 may include a machine-readable storage medium 728, on which is stored one or more set of instructions 722 (e.g., software) embodying any one or more of the methodologies of functions described herein, including instructions to cause the processing device 702 to execute a control system (e.g., control system 145). The instructions 722 may also reside, completely or at least partially, within the main memory 704 or within the processing device 702 during execution thereof by the computer system 700; the main memory 704 and the processing device 702 also constituting machine-readable storage media. The instructions 722 may further be transmitted or received over a network 720 via the network interface device 708.

The machine-readable storage medium 728 may also be used to store instructions to perform a method for device identification, as described herein. While the machine-readable storage medium 728 is shown in an exemplary embodiment to be a single medium, the term "machine-readable storage medium" should be taken to include a single medium or multiple media (e.g., a centralized or distributed database, or associated caches and servers) that store the one or more sets of instructions. A machine-readable medium includes any mechanism for storing information in a form (e.g., software, processing application) readable by a machine (e.g., a computer). The machine-readable medium may include, but is not limited to, magnetic storage medium (e.g., floppy diskette); optical storage medium (e.g., CD-ROM); magneto-optical storage medium; read-only memory (ROM); random-access memory (RAM); erasable programmable memory (e.g., EPROM and EEPROM); flash memory; or another type of medium suitable for storing electronic instructions.

The preceding description sets forth numerous specific details such as examples of specific systems, components, methods, and so forth, in order to provide a good understanding of several embodiments of the present disclosure. It will be apparent to one skilled in the art, however, that at least some embodiments of the present disclosure may be practiced without these specific details. In other instances, well-known components or methods are not described in detail or are presented in simple block diagram format in order to avoid unnecessarily obscuring the present disclosure. Thus, the specific details set forth are merely exemplary. Particular embodiments may vary from these exemplary details and still be contemplated to be within the scope of the present disclosure.

Reference throughout this specification to "one embodiment" or "an embodiment" means that a particular feature, structure, or characteristic described in connection with the embodiments included in at least one embodiment. Thus, the appearances of the phrase "in one embodiment" or "in an embodiment" in various places throughout this specification are not necessarily all referring to the same embodiment. In addition, the term "or" is intended to mean an inclusive "or" rather than an exclusive "or."

Additionally, some embodiments may be practiced in distributed computing environments where the machine-readable medium is stored on and or executed by more than one computer system. In addition, the information transferred between computer systems may either be pulled or pushed across the communication medium connecting the computer systems.

Embodiments of the claimed subject matter include, but are not limited to, various operations described herein. These operations may be performed by hardware components, software, firmware, or a combination thereof.

Although the operations of the methods herein are shown and described in a particular order, the order of the operations of each method may be altered so that certain operations may be performed in an inverse order or so that certain operation may be performed, at least in part, concurrently with other operations. In another embodiment, instructions or sub-operations of distinct operations may be in an intermittent or alternating manner.

The above description of illustrated implementations of the invention, including what is described in the Abstract, is not intended to be exhaustive or to limit the invention to the precise forms disclosed. While specific implementations of, and examples for, the invention are described herein for illustrative purposes, various equivalent modifications are possible within the scope of the invention, as those skilled in the relevant art will recognize. The words "example" or "exemplary" are used herein to mean serving as an example, instance, or illustration. Any aspect or design described herein as "example" or "exemplary" is not necessarily to be construed as preferred or advantageous over other aspects or designs. Rather, use of the words "example" or "exemplary" is intended to present concepts in a concrete fashion. As used in this application, the term "or" is intended to mean an inclusive "or" rather than an exclusive "or". That is, unless specified otherwise, or clear from context, "X includes A or B" is intended to mean any of the natural inclusive permutations. That is, if X includes A; X includes B; or X includes both A and B, then "X includes A or B" is satisfied under any of the foregoing instances. In addition, the articles "a" and "an" as used in this application and the appended claims should generally be construed to mean "one or more" unless specified otherwise or clear from context to be directed to a singular form. Moreover, use of the term "an embodiment" or "one embodiment" or "an implementation" or "one implementation" throughout is not intended to mean the same embodiment or implementation unless described as such. Furthermore, the terms "first," "second," "third," "fourth," etc. as used herein are meant as labels to distinguish among different elements and may not necessarily have an ordinal meaning according to their numerical designation.

What is claimed is:

1. A portable sterilization and decontamination system, comprising:
   a fuel cell to generate electricity and at least one of water or water vapor;
   a heating system operatively coupled to the fuel cell, the heating system to convert the electricity generated by the fuel cell to heat and provide the heat to a determined volume;
   a humidifying system operatively coupled to the fuel cell and powered by the electricity generated by the fuel cell, the humidifying system to utilize the electricity and the at least one of water or water vapor generated by the fuel cell to produce moisture and provide the moisture to the determined volume;
   a heat transfer system operatively coupled to the fuel cell and powered by the electricity generated by the fuel cell, the heat transfer system to move additional heat generated as a byproduct of the fuel cell to the determined volume; and
   a control system operatively coupled to the fuel cell, the heating system, the heat transfer system, and the humidifying system, the control system to monitor and control the fuel cell, the heating system, the heat transfer system, and the humidifying system.

2. The portable sterilization and decontamination system of claim 1, further comprising:
   one or more temperature sensors operatively coupled to the control system, the one or more temperature sensors being configured to measure a temperature associated with the determined volume; and
   one or more humidity sensors operatively coupled to the control system, the one or more humidity sensors being configured to measure a humidity associated with the determined volume.

3. The portable sterilization and decontamination system of claim 1, further comprising a lighting system operatively coupled to the fuel cell and the control system, the lighting system to convert the electricity to ultraviolet light and provide the ultraviolet light to the determined volume.

4. The portable sterilization and decontamination system of claim 1, wherein the heating system comprises an induction heater to generate the heat by electromagnetic induction.

5. The portable sterilization and decontamination system of claim 1, wherein the heating system comprises an electric resistance heater.

6. The portable sterilization and decontamination system of claim 1, further comprising:
   a fan system operatively coupled to the fuel cell, the fan system to move heated air produced by the fuel cell.

7. The portable sterilization and decontamination system of claim 1, further comprising:
   a reformer operatively coupled to the fuel cell, the reformer to extract hydrogen from hydrocarbon fuel and provide the extracted hydrogen to the fuel cell.

8. The portable sterilization and decontamination system of claim 1, further comprising:
   a communications system operatively coupled to the control system, the communications system to transmit and receive parameters associated with the portable sterilization and decontamination system.

9. The portable sterilization and decontamination system of claim 1, further comprising:
   an insulated chamber operatively coupled to the humidifying system, the insulated chamber to receive the moisture from the humidifying system.

10. The portable sterilization and decontamination system of claim 1, wherein at least a portion of the portable sterilization and decontamination system is coupled to a portable chassis.

11. The portable sterilization and decontamination system of claim 1, wherein the heating system comprises a radiant heater.

12. The portable sterilization and decontamination system of claim 1, wherein the heating system comprises a convection heater.

13. The portable sterilization and decontamination system of claim 1, wherein the heating system comprises a heat pump.

14. The portable sterilization and decontamination system of claim 1, wherein the humidifying system comprises a boiler.

15. The portable sterilization and decontamination system of claim 1, wherein the humidifying system comprises a membrane humidifier.

16. The portable sterilization and decontamination system of claim 3, wherein the lighting system comprises an ultraviolet germicidal irradiation system.

* * * * *